US009427262B2

(12) United States Patent
Iott et al.

(10) Patent No.: US 9,427,262 B2
(45) Date of Patent: Aug. 30, 2016

(54) METHOD FOR STABILIZING THE SPINE

(71) Applicant: GLOBUS MEDICAL, INC., Audubon, PA (US)

(72) Inventors: Andrew Iott, Villanova, PA (US); Prakash Sampath, Lincoln, RI (US)

(73) Assignee: Globus Medical, Inc., Audubon, PA (US)

( * ) Notice: Subject to any disclaimer, the term of this patent is extended or adjusted under 35 U.S.C. 154(b) by 118 days.

(21) Appl. No.: 14/326,033

(22) Filed: Jul. 8, 2014

(65) Prior Publication Data

US 2015/0012044 A1 Jan. 8, 2015

Related U.S. Application Data

(63) Continuation of application No. 13/731,558, filed on Dec. 31, 2012, now Pat. No. 8,808,332, which is a continuation of application No. 12/982,402, filed on Dec. 30, 2010, now Pat. No. 8,366,750, which is a continuation of application No. 12/014,025, filed on Jan. 14, 2008, now Pat. No. 7,892,258.

(51) Int. Cl.
*A61B 17/88* (2006.01)
*A61B 17/70* (2006.01)
*A61B 17/56* (2006.01)

(52) U.S. Cl.
CPC ....... *A61B 17/7052* (2013.01); *A61B 17/7002* (2013.01); *A61B 2017/564* (2013.01)

(58) Field of Classification Search
CPC .................. A61B 17/7052; A61B 17/7002
USPC .......... 606/246, 250–264, 278, 279
See application file for complete search history.

(56) References Cited

U.S. PATENT DOCUMENTS

| 5,312,405 A | * | 5/1994 | Korotko | A61B 17/7052 606/252 |
| 5,669,910 A | * | 9/1997 | Korhonen | A61B 17/7052 606/151 |
| 6,113,600 A | * | 9/2000 | Drummond | A61B 17/7049 606/250 |
| 6,749,614 B2 | | 6/2004 | Teitelbaum et al. | |
| 6,872,208 B1 | | 3/2005 | McBride et al. | |
| 8,021,398 B2 | | 9/2011 | Sweeney et al. | |
| 2006/0241602 A1 | | 10/2006 | Jackson | |
| 2007/0233090 A1 | | 10/2007 | Naifeh et al. | |
| 2007/0233094 A1 | * | 10/2007 | Colleran | A61B 17/7007 606/86 A |

FOREIGN PATENT DOCUMENTS

EP 0451765 A1 10/1991

* cited by examiner

*Primary Examiner* — Pedro Philogene
*Assistant Examiner* — David C Comstock

(57) ABSTRACT

Spine stabilization systems and integrated rods are disclosed. One spine stabilization system disclosed has at least four bone anchors and a stabilization member attached to the bone anchors. The stabilization member has first and second elongate portions interconnected by a connector portion. The first and second elongate members extend longitudinally and generally parallel to a central longitudinal axis and connector portion extends transverse to the central longitudinal axis from a first lateral end to a second lateral end. The connector portion is integrally connected to the first and second elongate portions such that there is no relative movement between the lateral ends and the respective elongate portion to which each end is attached.

20 Claims, 6 Drawing Sheets

METHOD FOR STABILIZING THE SPINE

CROSS REFERENCE TO RELATED APPLICATIONS

This Patent Application is a continuation of U.S. Ser. No. 13/731,558, filed Dec. 31, 2012, which is a continuation of U.S. patent application Ser. No. 12/982,402, filed Dec. 30, 2010, now issued as U.S. Pat. No. 8,366,750, which is a continuation of U.S. patent application Ser. No. 12/014,025, filed on Jan. 14, 2008, now issued as U.S. Pat. No. 7,892,258, the entire contents of which are incorporated by reference.

FIELD OF THE INVENTION

The present invention generally relates to a spine stabilization system. In particular, certain embodiments are directed to an integrated stabilization member having increased torsional strength.

BACKGROUND OF THE INVENTION

The human spine is particularly important because it protects the spinal cord, which is responsible for relaying electrical impulses from the brain to the rest of the body. Occasionally, an accident or other outside force may cause the vertebrae which make up the spine to be broken, cracked, or chipped. Each of these situations are dangerous, and are handled by the most skilled physicians and surgeons. The remedy for a broken, cracked, or chipped bone may be different for every individual, and may change according to the situation under which the injury occurred.

One situation that commonly arises occurs is when vertebrae or portions of vertebrae or spine are broken, cracked, or are beginning to fail to function normally. One treatment technique used by doctors to remedy this situation involves using a pair of rods that are connected to several vertebrae. The rods may be aligned along the periphery of the vertebrae, and are typically used to maintain the alignment of the bones. This may allow the vertebrae to re-grow bony tissue or cartilage. In addition, aligning the vertebrae allows them to heal properly, and prevents movement of the spine from injuring the spinal cord.

In order to prevent the movement of the spine, a fixation system is often used to hold the two rods together. The fixation system allows the rods to be fixed in place under normal conditions. Many fixation devices are currently available. They vary in shape, size, and their approach to preventing the rods from moving. One type of device that has been used involves a single connection body that ties in between the two rods, over the body of the vertebrae. Though this device serves the purpose of preventing the rods from moving, it also has several disadvantages. For example, many of these devices are unable to move, rendering them unable to adapt to the contour of the spine. Another limitation of these devices is that they typically do not allow for clearance of the body of the vertebrae, which can cause damage to the vertebrae or cause the device to protrude from underneath a person's skin.

Many devices hold the rods in place by gripping them from the outer portion of the bars. These devices also achieve the purpose of holding the bars in place, but have several limitations. For instance, these devices often may not be capable of achieving the same degree of grip on the rods as compared to a configuration that grips the bars from the inner area, between the bars.

Other devices have aimed to eliminate the limitations of their predecessors by providing two connecting bodies that have a small degree of adjustability. However, many of these devices are unable to translate axially, which prevents them from adjusting to the spacing between the rods. Other devices are unable to rotate to adjust for rods that aren't coplanar. Additionally, these devices often do not have the ability to rotate freely, preventing them from adjusting to the contours of the spine. Devices such as these may provide greater adjustability at the expense of increased complexity, number of components, increased overall height, or other limitations and disadvantages.

A continuing need exists for a spinal fixation system that is able to adjust the contours of the spine, is simple to install and meets the demanding mechanical loads that are experienced when implanted in a patient.

BRIEF DESCRIPTION OF THE DRAWINGS

Spine stabilization systems and integrated rods are disclosed. One spine stabilization system has at least four bone anchors and a stabilization member attached to the bone anchors. The stabilization member has first and second elongate portions interconnected by a connector portion. The first and second elongate members extend longitudinally and generally parallel to a central longitudinal axis and connector portion extends transverse to the central longitudinal axis from a first lateral end to a second lateral end. The connector portion is integrally connected to the first and second elongate portions such that there is no relative movement between the lateral ends and the respective elongate portion to which each end is attached.

In one variation, the width of the connector portion adjacent to the elongate portions is less than 5 mm when viewed from the side. In another variation, the connecting portion is fixably telescopingly extendable in the lateral direction transverse to the central longitudinal axis to selectably vary the lateral separation of the elongate portions and all other degrees of freedom are fixed.

BRIEF DESCRIPTION OF THE DRAWINGS

Figure 1:
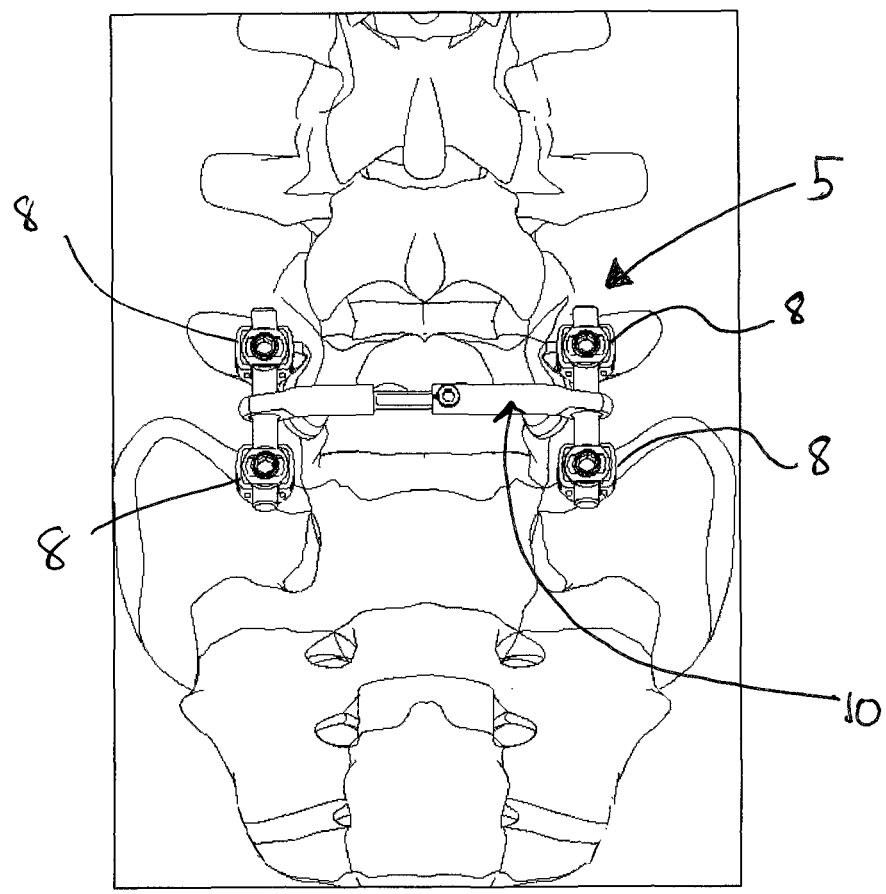
Figure 3:
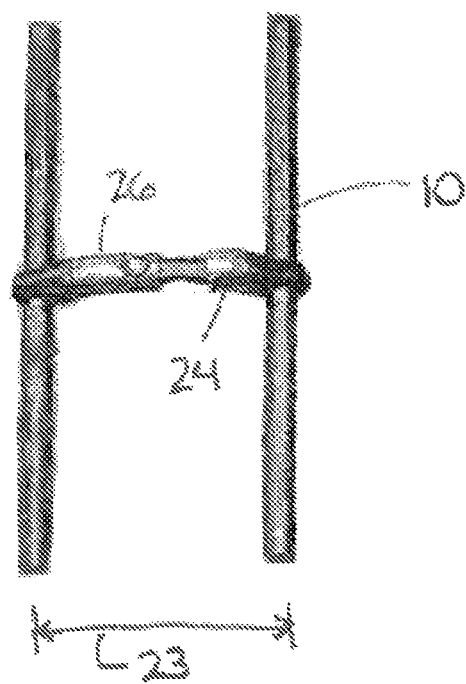
Figures 2, 4:
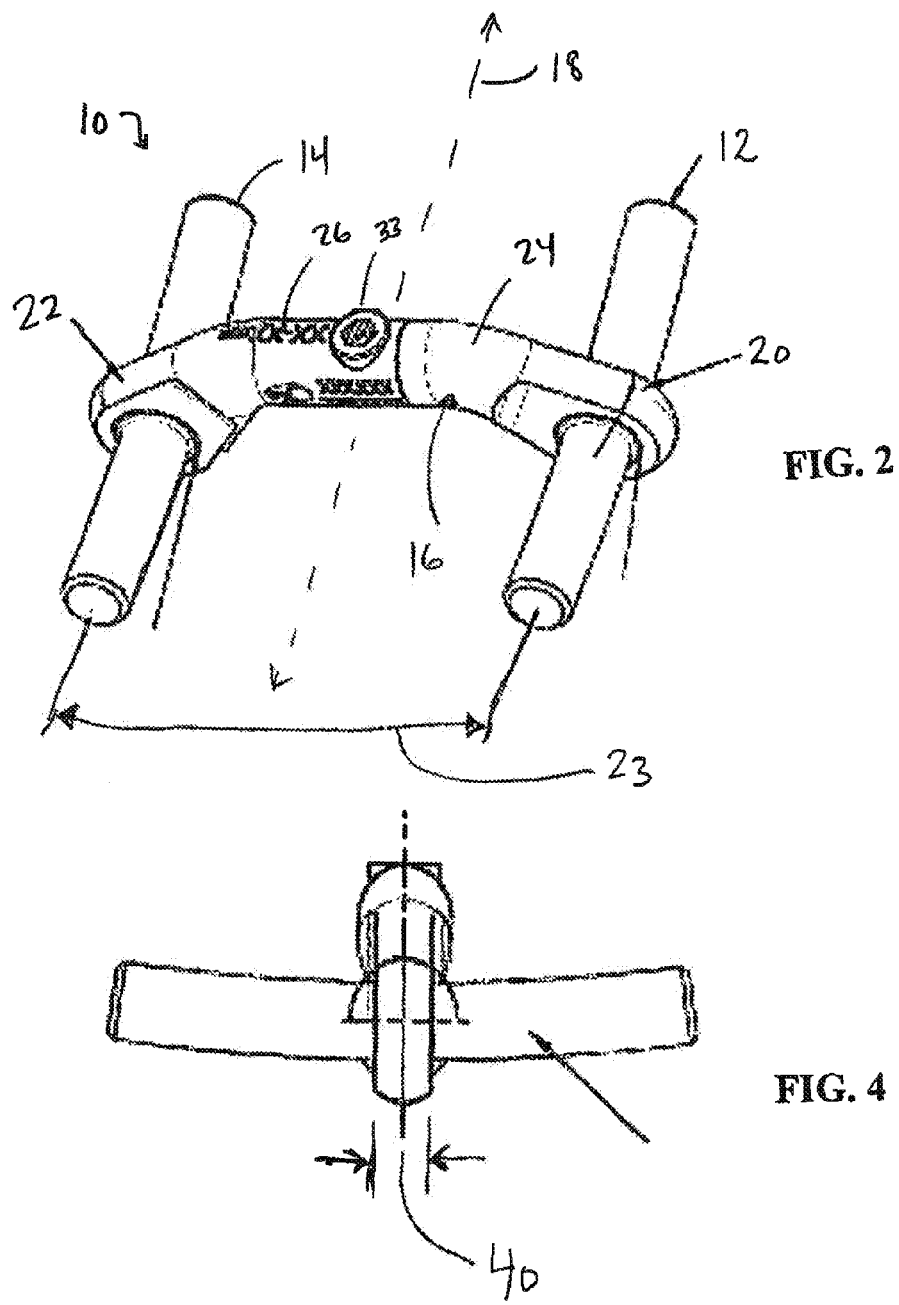
Figure 5:
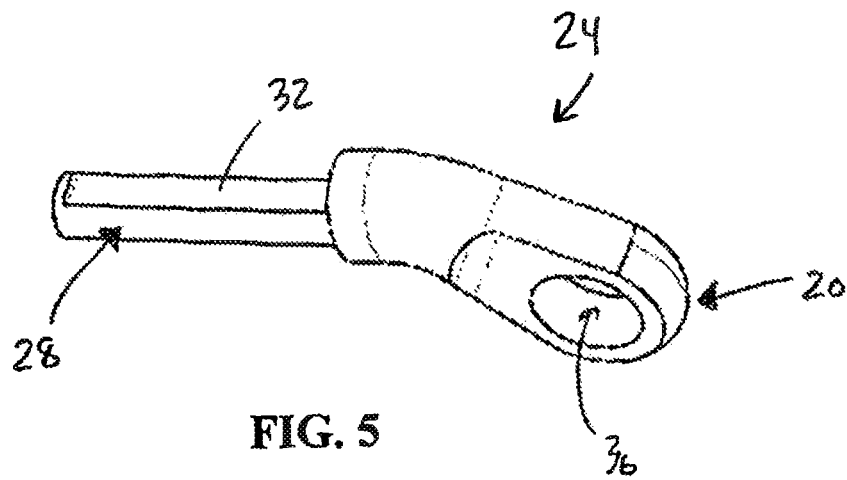
Figure 6:
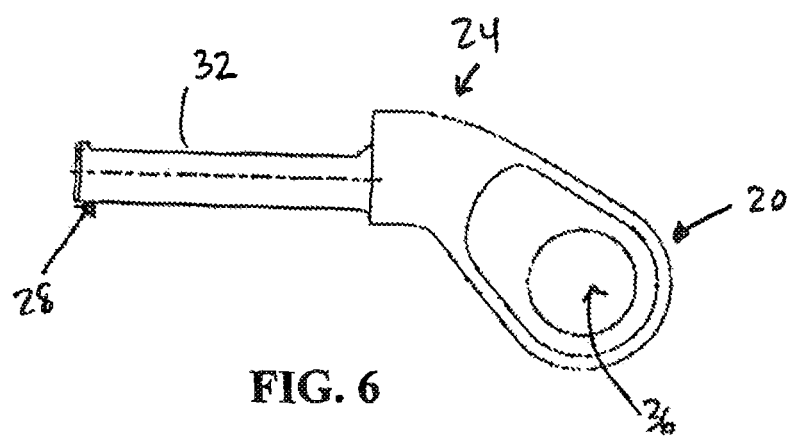
Figure 7:
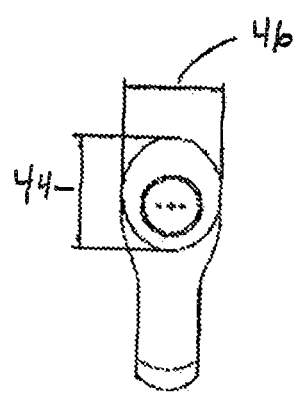
Figure 8:
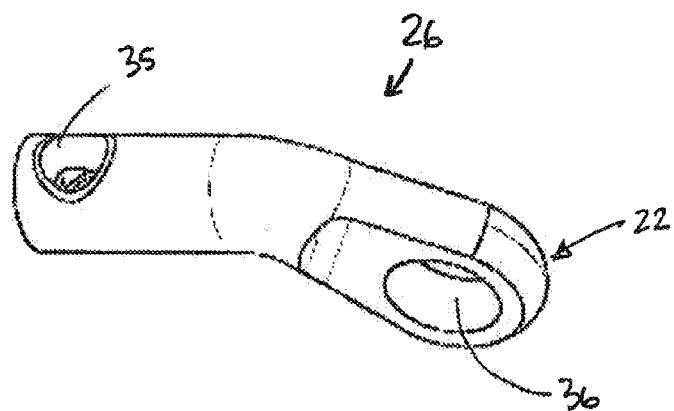
Figure 9:
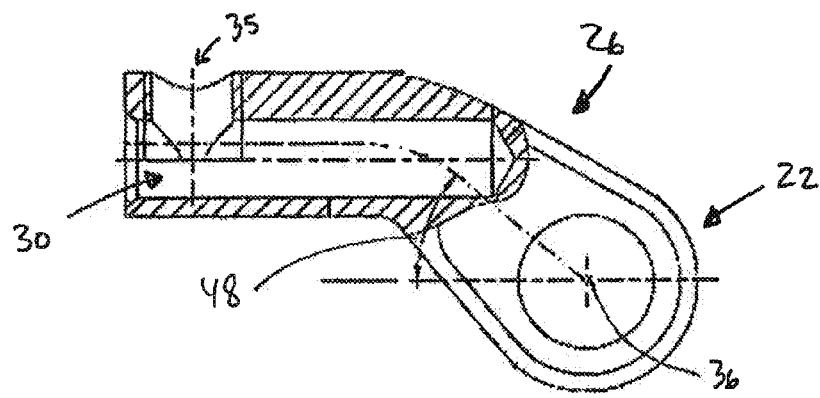
Figure 10:
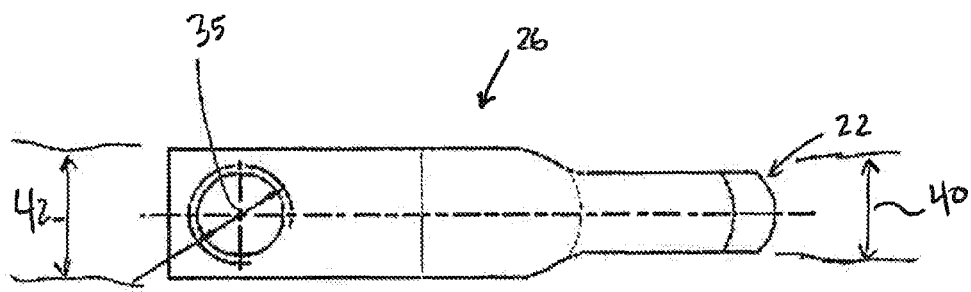
Figure 11:
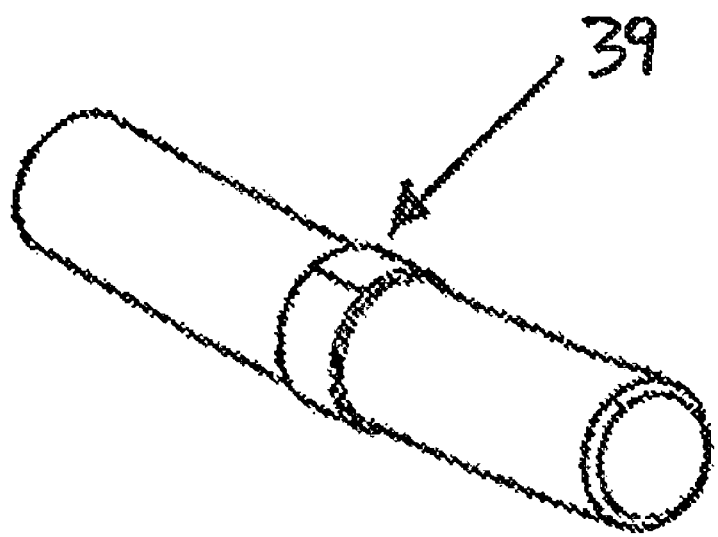
Figure 12:
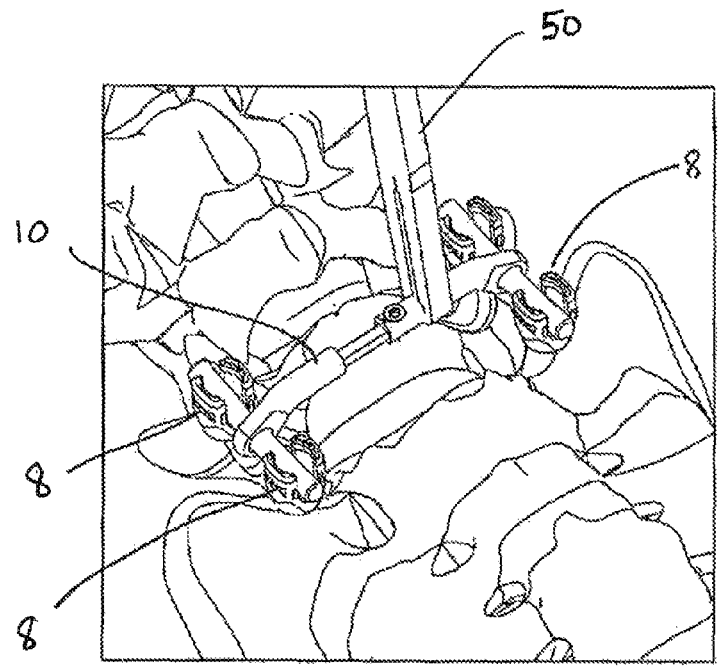
Figure 13:
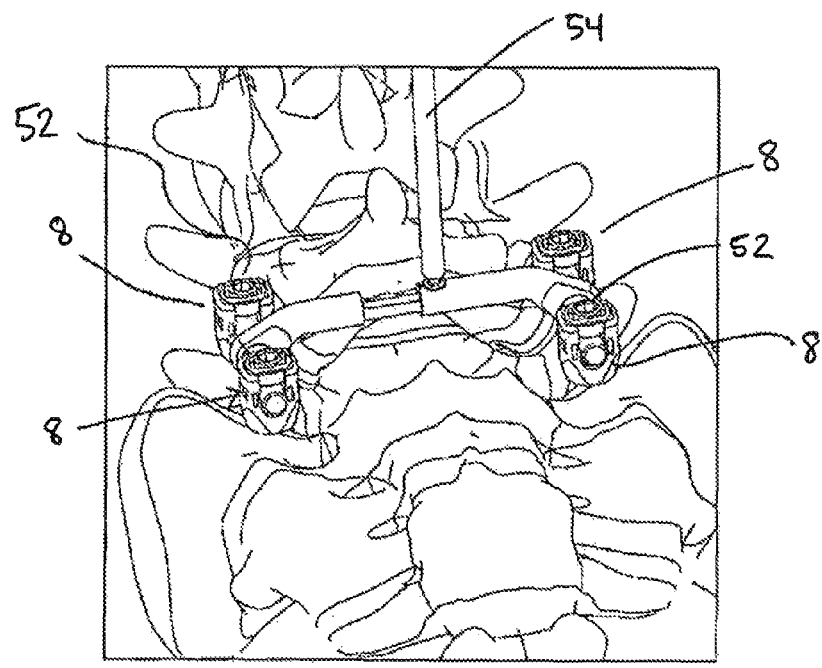

FIG. 1 is a perspective view of one embodiment of a stabilization system according to the invention;

FIG. 2 is a perspective view of one embodiment of a stabilization member of the system of FIG. 1;

FIG. 2 is a perspective view of one embodiment of a stabilization member of the system of FIG. 1;

FIG. 3 is a perspective view of the stabilization member of FIG. 2 shown in a laterally expanded condition;

FIG. 4 is a side view of the stabilization member of FIG. 2;

FIGS. 5-7 are perspective, front, and side views of one embodiment of an arm of a connector portion of the stabilization member of FIG. 2;

FIGS. 8-10 are perspective, partial cross-section front, and side views of another embodiment of an arm of a connector portion of the stabilization member of FIG. 2;

FIG. 11 is a perspective view of one embodiment of an elongate member of the stabilization member of FIG. 2;

FIG. 12 depicts one step in an embodiment of a method of installation of a stabilization system according to the invention; and FIG. 13 depicts another step in an embodiment of a method of installation of a stabilization system according to the invention.

DETAILED DESCRIPTION OF THE ILLUSTRATED EMBODIMENTS

Embodiments of the present invention are generally directed to a spine stabilization system. In particular, certain embodiments are directed to an integrated stabilization member having increased torsional strength.

Referring now to FIG. 1, one embodiment of a stabilization system 5 according to the invention is shown. Stabilization system 5 generally comprises four bone anchors 8 attached to bone and a stabilization member 10 rigidly attached to the bone anchors. As best seen in FIG. 2, stabilization member 10 generally comprises first and second elongate members or rods 12, 14 interconnected by connector portion 16. In one variation, first and second elongate members extend longitudinally and generally parallel to a central longitudinal axis 18 and connector portion 16 extends transverse and generally perpendicular to axis 18. In this regard, when stabilization member 10 is viewed from the top, such as when viewed as implanted in a patient as shown in FIG. 1, it has a general H-like shape.

The opposing ends 20, 22 of connector portion 16 are generally rigidly or fixedly connected to elongate members 12, 14 such that there is no relative movement between the ends 20, 22 and the respective elongate members 12, 14 to which each end is attached. In one variation, elongated members 12, 14 and connector portion 16 may be a unitary construction manufactured from the same block of material. In another embodiment, connector portion 16 may be manufactured to be immovably connected to elongate members 12, 14 by welding. In one variation, a laser weld may be used to fix connector portion 16 to elongate members 12, 14. In this regard, as shown in FIG. 2, ends 20, 22 of connector portion 16 may extend around the entire periphery of elongate members 12, 14 and a 360° weld may be applied to attach connector portion 16 to elongate members 12, 14.

Referring to FIGS. 2-3, in one embodiment connector portion may provide for telescoping movement in the lateral direction transverse to axis 18. In this regard, elongate members 12, 14 may be variably spaced laterally apart to accommodate patient anatomy. In one embodiment, the lateral length 23 of connector portion 16 may be selectively varied between about 30 mm and 90 mm, and in another embodiment the lateral length may be adjustable between about 38 mm and 71 mm. In this regard, according to this variation, the only relative movement between the elongate elements is lateral movement with all other degrees of freedom fixed. One skilled in the art may appreciate the simplicity involved with such limited adjustability as less fidgeting is required to install the stabilization member. Also, such a streamlined design may decrease operating time by reducing insertion steps since a surgeon does not need to separately attach a transconnector device in situ.

In one embodiment of a laterally telescoping stabilization member 10, connector portion 16 comprises an extender arm portion 24 telescopingly received within a receiver arm portion 26. Referring to FIGS. 5-6, extender arm portion 24 of connector 16 generally comprises an elongate shaft portion 28 extending medially opposite lateral end 20. Shaft portion 28 is configured and dimensioned to be received within channel 30 which extends medially within receiver arm portion 26. In one variation, a generally flattened upper surface 32 extends along at least part of shaft portion 28 to facilitate a set screw 33 to fixedly clamp the shaft portion of extender arm 24 within the channel 30 of receiver arm 26. As seen in FIGS. 8-10, a hole 35 may be provided to accommodate the set screw such that the extent of lateral offset may be fixedly adjusted. In alternative embodiments, alternative adjustable telescoping means known to those skilled in the art may be provided to facilitate lateral adjustability of the elongate members 10, 12.

Referring to FIGS. 5-6 and 8-9, according to one embodiment, the lateral ends 20, 22 respectively of connector portion 16 comprise an eyelet or through hole 36 to receive an elongate member therethrough. In one variation, hole 36 may be generally cylindrical and may have a diameter slightly larger than the elongate member to which it is to attach. In this regard, referring to FIG. 11, elongate members 12, 14 may have a radially raised section 39 with additional material or larger diameter region configured and dimensioned to interface with the interior region of hole 36. Such additional material may facilitate the welding attachment of the respective connector portion to the respective elongate member. For example, since the junction between the connector portion and the additional material is slightly spaced from the perimeter of the elongated element, the rod is less of a direct heat sink during the welding process which ends up requiring less energy during the weld and provides for efficient manufacturing. The additional material provided adjacent the weld junction may also allow for the creation of a fillet around the entire periphery of the elongate member thereby creating a strong mechanical joint resistant to high torsional loads.

Referring to FIG. 10, in another aspect of the invention, the width 40 profile of the connector portion 16 adjacent to the elongate elements 12, 14 when viewed from the side is smaller than width profile 42 of the connector portion 16 spanning between the elongate members. In this regard, the narrowing of the connector portion 16 provides a smaller run on the rod, as best seen in FIG. 4, than would be possible without such narrowing. In other words, less space is taken up along the length of the elongate members 10, 12 to accommodate the attachment of connector portion 16 thereto. For example, as best seen in FIG. 4, according to one embodiment the width 40 along the rod is less than 5 mm and in other embodiments the width is less than 4 mm. Those skilled in the art will appreciate that with such a smaller run on the rod, the spacing of adjacent anchor members may be commensurately shortened. Such a feature may be advantageous, for example, in procedures where the anchors are typically inserted with such a small separation distance, such as the fixation of the L5-S1 segment.

In one embodiment, best shown in FIG. 7, the cross-section of the central portion of connector 16 is generally ovoid having a height 44 that is between about 6 mm and 9 mm and a width 46 that is between about 5 mm and 8 mm. In one embodiment, height 44 is about 7.5 mm and width 46 is about 6.5 mm. However, the precise geometry is not critical and in alternative exemplary embodiments, the central portion of connector 16 may have a hexagonal, cylindrical, square, or any other geometric cross-section as those skilled in the art may contemplate. In another aspect of the invention, best shown in FIG. 9, the lateral ends 20, 22 of connector portion 16 may be angled upwards from the rod to accommodate the natural anatomy such that the connector portion may extend over posterior elements of the spine. In one embodiment, the angle 48 may be between about 20 and 60 degrees and in another embodiment angle 48 may be about 40 degrees.

According to some embodiments, as shown in FIG. 1, elongate members 12, 14 may have a generally circular cross-section. In one variation, elongate members 12, 14 may comprise a rod having a circular cross-section between about 5 mm and 7 mm, and in particular between about 5.5 mm and 6.35 mm. However, the precise geometry is not critical and in alternative exemplary embodiments, elongate members 12, 14 may have a hexagonal, elliptical, square, or any other geometric cross-section as those skilled in the art may contemplate. Also, elongate members 12, 14 need not have the same cross-section, nor is it necessary that the cross-sections be uniform along the length. Elongate members 12, 14 may be provided in a wide variety of lengths and profiles. For example according to one variation, elongate members 12,14 may be provided in lengths ranging from about 30 mm to about 120 mm and in other embodiments lengths between about 40 mm and 100 mm may be provided. Similarly, elongate members may be bent or contoured to, for example, generally approximate the natural anatomy of the spine region where it is to be implanted, among other things. In this regard, elongate elements 12, 14 may be pre-contoured or bent by a physician in situ. For example, as shown in FIGS. 1 and 2, stabilization member 10 is shown with a generally curved profile with connector portion 16 extending across the concave side of elongate members 12, 14. Again the lengths and profiles need not be the same for each elongate member 12, 14.

Referring now to FIGS. 12-13, one embodiment of a method of installation is shown. According to one variation, anchors or bone screws are inserted into pedicles of the thoracolumbar and/or sacral spine. In one method, four bone screws 8 are inserted into the four adjacent pedicles to one spinal segment, such as for example between the L5 and S1 spinal segment. Attachment of the stabilization member 10 to the pedicle screws is dependent on the pedicle screws used in the construct. The size and number of screws are dependent on the length and location of the stabilization member 10.

In another variation, the appropriate rod contour and length of the stabilization member 10 may be determined using a rod template. If necessary, one or both of the elongate members or rods 12, 14 may be bent or contoured using a rod bender. A rod cutter may also be used to cut the implant to the appropriate length.

As shown in FIG. 12, the integrated stabilization member 10 may be top loaded into the screw heads using a rod holder 50. Once loaded into the screw heads, the stabilization member 10 may be secured to the pedicle screws 8. In one method, a locking cap driver may be used to install a locking cap 52. The driver may be rotated to engage the locking cap 52 into the screw head and capture the elongate members 12, 14 of stabilization member 10. A set screw within the locking cap may be tightened to secure the construct. As shown in FIG. 13, the lateral offset of rods 12, 14 may be secured by tightening the set screw 33 using a driver 54.

Stabilization members 10 according to the invention may comprise any material, or combination of materials suitable for implantation in the human body. The materials may include, but are not limited to, a metal or alloy. In some embodiments, steel, titanium, iron, and the like may be used. The type of material that is used may be chosen such that it has sufficient strength to maintain the elongate members 12, 14 in a substantially fixed manner under normal conditions. Normal conditions, as described, will be understood to be conditions that a healthy spine may be subjected to without causing the structural integrity of the vertebrae to be compromised. For example, it is estimated that the torsional stiffness of the human thoracolumbar spine is about 1.2 N-m per degree of axial rotation and cyclical torsional loads producing more than +/−1.5° of angular displacement per spinal segment are detrimental to elements of the lumbar spine. As a result, it is estimated that the maximum torque that will be effectively resisted by the thoracolumbar spine is about 1.8 N-m. Thus, using a material that is capable of maintaining its structural integrity when subjected to the conditions present inside the human body is desired. In one embodiment, stabilization member 10 is made from a titanium alloy and the torsional stiffness is at least 4 N-m/degree. Those skilled in the art may appreciate that such a relatively increased torsional stiffness may reduce torsional load on screws, minimizing the risk of construct breakdown.

Example

In a static torsional test method used conforming to ASTM standard F1717, five constructs similar to that shown in FIG. 1 (i.e. with a stabilization member 10 attached to four anchors) were tested. Torque and angular displacement were recorded. Static torsional tests were performed in displacement control at a rate of 30°/min, starting at zero torque and ending at failure of a maximum angular displacement of 60°. Yield load was calculated using the 2% offset yield criterion, per the ASTM standard F1717. All five specimens were tested in static torsion and exhibited an average torsional stiffness of 5.7 N-m/Degree. A similar construct without a transconnector was also tested using the same methods and exhibited an average torsional stiffness of 1.9 N-m/Degree and another construct having a non-integrated conventional transconnector exhibited a torsional stiffness of 3.4 N-m/Degree using the same test.

While it is apparent that the invention disclosed herein is well calculated to fulfill the objects stated above, it will be appreciated that numerous modifications and embodiments may be devised by those skilled in the art.

What is claimed is:

1. A surgical method comprising:
   inserting a first anchor into a first pedicle adjacent to one spinal segment;
   inserting a second anchor into a second pedicle adjacent to the one spinal segment;
   inserting a third anchor into a third pedicle adjacent to the one spinal segment;
   inserting a fourth anchor into a fourth pedicle adjacent to the one spinal segment; and
   attaching a stabilization member into each of the first, second, third and fourth anchors, wherein the stabilization member comprises:
   a first elongate member;
   a second elongate member; and
   a connector portion between the first elongate member and the second elongate member, wherein the connector portion comprises a first end having a first opening for receiving the first elongate member and a second end having a second opening for receiving the second elongate member, and wherein the first end of the connector portion has a first width profile adjacent to the first elongate member that is smaller than a second width profile that is further removed from the first elongate member.

2. The surgical method of claim 1, wherein the second end of the connector portion has a first width profile adjacent to the second elongate member that is smaller than a second width profile that is further removed from the first second member.

3. The surgical method of claim 1, wherein at least one of the first opening and the second opening extends around an entire periphery of the first elongate member or the second elongate member.

4. The surgical method of claim 1, wherein the first elongate member, second elongate member, and connector portion are formed by a unitary construction from the same block of material.

5. The surgical method of claim 1, wherein the first elongate member and the second elongate member are each welded to the connector portion.

6. The surgical method of claim 5, wherein the weld between the first elongate member and the connector portion is a 360 degree weld that extends around an entire periphery of the first elongate member.

7. The surgical method of claim 1, wherein a cross-sectional portion of the connector is generally ovoid.

8. The surgical method of claim 1, wherein the one spinal segment is located in the thoracolumbar region of the spine.

9. The surgical method of claim 1, wherein the one spinal segment is located between the L5 and S1 spinal segment.

10. A surgical method comprising:
  inserting a first anchor into a first pedicle adjacent to one spinal segment;
  inserting a second anchor into a second pedicle adjacent to the one spinal segment;
  inserting a third anchor into a third pedicle adjacent to the one spinal segment;
  inserting a fourth anchor into a fourth pedicle adjacent to the one spinal segment; and
  attaching a stabilization member into each of the first, second, third and fourth anchors, wherein the stabilization member comprises:
    a first elongate member;
    a second elongate member; and
    a telescoping connector portion between the first elongate member and the second elongate member, wherein the telescoping connector portion comprises an extender arm portion having a first opening for receiving the first elongate member and a receiver arm portion having a second opening for receiving the second elongate member, and wherein the extender arm portion of the connector portion has a first width profile adjacent to the first elongate member that is smaller than a second width profile that is further removed from the first elongate member.

11. The surgical method of claim 10, wherein the receiver arm portion of the connector portion has a first width profile adjacent to the second elongate member that is smaller than a second width profile that is further removed from the second elongate member.

12. The surgical method of claim 10, wherein the extender arm portion comprises an elongated shaft portion with flattened surfaces.

13. The surgical method of claim 10, wherein the telescoping connector further comprises a screw to secure the extender arm portion within the receiver arm portion.

14. The surgical method of claim 10, wherein the telescoping connector comprises a first end having a first opening for receiving the first elongate member and a second end having a second opening for receiving the second elongate member.

15. The surgical method of claim 14, wherein the first opening extends completely around a circumference of the first elongate member.

16. The surgical method of claim 15, wherein the first opening is welded 360 degrees around the first elongate member.

17. The surgical method of claim 10, wherein the one spinal segment is within the thoracolumbar region of the spine.

18. The surgical method of claim 10, wherein the one spinal segment is between the L5-S1 region of the spine.

19. The surgical method of claim 10, wherein the first elongate member is of a different width from the second elongate member.

20. The surgical method of claim 10, wherein the connector has a cross-section that is ovoid in shape.

* * * * *